United States Patent [19]
Knauf-Beiter et al.

[11] Patent Number: 5,998,455
[45] Date of Patent: Dec. 7, 1999

[54] CROP PROTECTION COMPOSITIONS

[75] Inventors: Gertrude Knauf-Beiter, Müllheim, Germany; Ruth Beatrice Küng, Allschwil, Switzerland

[73] Assignee: Novarits Crop Protection, Inc., Greensboro, N.C.

[21] Appl. No.: 08/981,437

[22] PCT Filed: Jun. 4, 1996

[86] PCT No.: PCT/EP96/02423

§ 371 Date: Dec. 16, 1997

§ 102(e) Date: Dec. 16, 1997

[87] PCT Pub. No.: WO97/00012

PCT Pub. Date: Jan. 3, 1997

[30] Foreign Application Priority Data

Jun. 16, 1995 [CH] Switzerland ............ 1785/95

[51] Int. Cl.⁶ .......... A01N 37/12; A01N 37/44; A01N 43/64
[52] U.S. Cl. .............. 514/383; 514/539
[58] Field of Search ............ 514/539, 383

[56] References Cited

U.S. PATENT DOCUMENTS

| | | | |
|---|---|---|---|
| 5,286,724 | 2/1994 | Sauter et al. | 514/231.2 |
| 5,317,027 | 5/1994 | Sauter et al. | 514/399 |
| 5,464,839 | 11/1995 | Wingert et al. | 514/256 |
| 5,476,868 | 12/1995 | Wingert et al. | 514/383 |

FOREIGN PATENT DOCUMENTS

| | | |
|---|---|---|
| 78167/91 | 12/1991 | Australia . |
| 2005345-3 | 6/1990 | Canada . |
| 370629 | 5/1990 | European Pat. Off. . |
| 0 460 575 | 12/1991 | European Pat. Off. . |
| 0 524 496 | 1/1993 | European Pat. Off. . |
| 0 531 837 | 3/1993 | European Pat. Off. . |
| 0 645 084 | 3/1995 | European Pat. Off. . |
| 0 645 091 | 3/1995 | European Pat. Off. . |
| 90 07493 | 7/1990 | WIPO . |

*Primary Examiner*—Allen J. Robinson
*Attorney, Agent, or Firm*—Michael P. Morris; John D. Peabody, III

[57] ABSTRACT

A plant-microbicidal composition comprising at least two active ingredient components in an amount that achieves a synergistic effect, together with a suitable carrier, wherein component I is a compound of formula (I) wherein: X is CH or N; R is $CH_3$ or cyclopropyl; Y is H, F, Cl, Br, $CF_3$, $CF_3O$ or propargyloxy; Z is H, F, Cl, $CF_3$ or $CF_3O$; or Y and Z together form a methylenedioxy group, a (difluoromethylene)dioxy group, an ethylenedioxy group, a (trifluoroethylene)dioxy group or a benzo group; and wherein component II is a compound selected from the group propiconazol, difenoconazol, penconazol, tebuconazol, epoxyconazol, cyproconazol, hexaconazol, fenbuconazoi, flusilazol, metconazol, tetraconazol, bromuconazol, fluquinconazol, prochloraz, pyrifenox and myclobutanil; or one of the salts or metal complexes thereof.

8 Claims, No Drawings

CROP PROTECTION COMPOSITIONS

This application is a 371 of PCT/EP96/02423, filed Jun. 4, 1996.

The present invention relates to novel crop-protecting compositions having synergistically enhanced action, comprising at least two active ingredient components, and to methods of using such compositions in crop protection, especially of controlling and preventing attack by diseases.

Component I is a compound of formula I

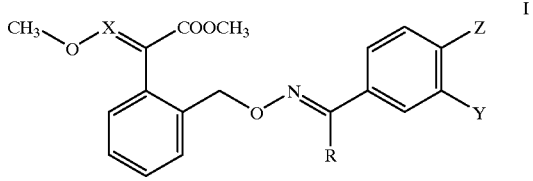

wherein:
X is CH or N;
R is $CH_3$ or cyclopropyl;
Y is H, F, Cl, Br, $CF_3$, $CF_3O$ or propargyloxy;
Z is H, F, Cl, $CF_3$ or $CF_3O$; or
Y and Z together form a methylenedioxy group, a (difluoromethylene)dioxy group, an ethylenedioxy group, a (trifluoroethylene)dioxy group or a benzo group.

Those compounds are described in EP-A-403 618, EP-A-460 575, WO 92/18494 and other publications.

Component II is a compound selected from the group
A) 1-[2-(2,4-dichlorophenyl)-4-propyl-1,3-dioxolan-2-ylmethyl]-1H-1,2,4-triazole ("propiconazol"), (reference: GB-1 522 657);
B) 1-{2-[2-chloro-4-(4-chlorophenoxy)-phenyl]-4-methyl-1,3-dioxolan-2-ylmethyl}-1H-1,2,4-triazole ("difenoconazol"), (reference: GB-2 098 607);
C) 1-[2-(2,4-dichlorophenyl)pentyl-1H-1,2,4-triazole ("penconazol") (reference: GB-1 589 852);
D) α-[2-(4-chlorophenyl)ethyl]-α-(1,1-dimethylethyl)-1H-1,2,4-triazole-1-ethanol ("tebuconazol"), (reference: EP-A-40 345);
E) 1-[[3-(2-chlorophenyl)-2-(4-fluorophenyl)oxiran-2-yl]methyl]-1H-1,2,4-triazole ("epoxyconazol"), (reference: EP-A-196 038);
F) α-(4-chlorophenyl)-α-(1-cyclopropylethyl)-1H-1,2,4-triazole-1-ethanol ("cyproconazol"), (reference: U.S. Pat. No. 4,664,696);
G) α-butyl-α-(2,4-dichlorophenyl)-1H-1,2,4-triazole-1-ethanol ("hexaconazol"), (reference: GB-2 119 653);
H) 4-(4-chlorophenyl)-2-phenyl-2-(1,2,4-triazol-1-ylmethyl)-butyronitrile ("fenbuconazol"), (reference: EP-A-251 775);
J) 1-{[bis(4-fluorophenyl)methylsilyl]methyl}-1H-1,2,4-triazole ("flusilazol"), (reference: U.S. Pat. No. 4,510,136);
K) 5-(4-chlorobenzyl)-2,2-dimethyl-1-(1H-1,2,4-triazol-1-ylmethyl)-cyclopentanol ("metconazol"), (reference: EP-A-267 778);
L) 2-(2,4-dichlorophenyl)-3-(1H-1,2,4-triazol-1-yl)propyl-1,1,2,2-tetrafluoroethyl ether ("tetraconazol"), (reference: EP-A-234 242);
M) 1-[4-bromo-2-(2,4-dichlorophenyl)tetrahydrofurfuryl]-1H-1,2,4-triazole ("bromuconazol"), (reference: EP-A-246 982);
N) 3-(2,4-dichlorophenyl)-6-fluoro-2-(1H-1,2,4-triazol-1-yl)quinazolin-4(3H)-one ("fluquinconazol"), (reference: EP-A-183 458);
O) N-propyl-N-[2-(2,4,6-trichlorophenoxy)ethyl] imidazole-1-carboxamide ("prochloraz"), (reference: U.S. Pat. No. 4,154,945);
P) 2',4'-dichloro-2-(3-pyridyl)acetophenone-O-methyloxime ("pyrifenox"), (reference: EP-A-49 854); and
Q) 2-p-chlorophenyl-2-(1H-1,2,4-triazol-1-ylmethyl) hexanenitrile ("myclobutanil"), (reference: R. Worthing (Ed.), The Pesticide Manula, 9th. edition, 1991, page 601), or one of the salts or metal complexes thereof.

The invention relates also to mixtures wherein in component I of formula I:
X is CH or N;
R is $CH_3$ or cyclopropyl;
Y is H, F, Cl, Br, $CF_3$, $CF_3O$ or propargyloxy;
Z is H, F or Cl; or
Y and Z together form a methylenedioxy group, a (difluoromethylene)dioxy group, an ethylenedioxy group, a (trifluoroethylene)dioxy group or a benzo group; and wherein component II is a compound selected from the group
A) 1-[2-(2,4-dichlorophenyl)-4-propyl-1,3-dioxolan-2-ylmethyl]-1H-1,2,4-triazole ("propiconazol");
B) 1-{2-[2-chloro-4-(4-chlorophenoxy)-phenyl]-4-methyl-1,3-dioxolan-2-ylmethyl}- 1H-1,2,4-triazole ("difenoconazol");
C) 1-[2-(2,4-dichlorophenyl)pentyl-1H-1,2,4-triazole ("penconazol");
D) α-[2-(4-chlorophenyl)ethyl]-α-(1,1-dimethylethyl)-1H-1,2,4-triazole-1-ethanol ("tebuconazol");
E) 1-[[3-(2-chlorophenyl)-2-(4-fluorophenyl)oxiran-2-yl]methyl]-1H-1,2,4-triazole ("epoxyconazol");
F) α-(4-chlorophenyl)-α-(1-cyclopropylethyl)-1H-1,2,4-triazole-1-ethanol ("cyproconazol");
G) α-butyl-α-(2,4-dichlorophenyl)-1H-1,2,4-triazole-1-ethanol ("hexaconazol");
H) 4-(4-chlorophenyl)-2-phenyl-2-(1,2,4-triazol-1-ylmethyl)-butyronitrile ("fenbuconazol");
J) 1-{[bis(4-fluorophenyl)methylsilyl]methyl}-1H-1,2,4-triazole ("flusilazol");
K) 5-(4-chlorobenzyl)-2,2-dimethyl-1-(1H-1,2,4-triazol-1-ylmethyl)-cyclopentanol ("metconazol");
L) 2-(2,4-dichlorophenyl)-3-(1H-1,2,4-triazol-1-yl)propyl-1,1,2,2-tetrafluoroethyl ether ("tetraconazol");
M) 1-[4-bromo-2-(2,4-dichlorophenyl)tetrahydrofurfuryl]-1H-1,2,4-triazole ("bromuconazol");
N) 3-(2,4-dichlorophenyl)-6-fluoro-2-(1H-1,2,4-triazol-1-yl)quinazolin-4(3H)-one ("fluquinconazol");
O) N-propyl-N-[2-(2,4,6-trichlorophenoxy)ethyl] imidazole-1-carboxamide ("prochloraz"); and
P) 2',4'-dichloro-2-(3-pyridyl)acetophenone-O-methyloxime ("pyrifenox"),
or one of the salts or metal complexes thereof.

It has now been found, surprisingly, that in the prevention and control of plant diseases, the mixtures of components I and II according to the invention exhibit not only additive action, but clearly synergistically enhanced action.

Advantageous mixing ratios of the two active ingredients are I:II=30:1 to 1:12, preferably I:II=20:1 to 1:5 and 10:1 to 1:3.

Especially advantageous mixing ratios are
I:IIA=10:1 to 1:5, especially 8:1 to 1:2
I:IIB=5:1 to 1:3
I:IIC=6:1 to 1:2
I:IID=10:1 to 1:4
I:IIE=10:1 to 1:5
I:IIF=8:1 to 1:4
I:IIG=6:1 to 1:2

I:IIH=10:1 to 1:5
I:IIJ=10:1 to 1:10
I:IIK=6:1 to 1:4
I:IIL=8:1 to 1:3
I:IIM=7:1 to 1:3
I:IIN=6:1 to 1:6
I:IIO=3:1 to 1:12
I:IIP=4:1 to 1:10
I:IIQ=8:1 to 1:3

Preference is given to two-component mixtures wherein component I is selected from the following compounds:

(01) 3-methoxy-2-[α-{[(α-cyclopropyl-3-trifluoromethyl-benzyl)imino]-oxy}-o-tolyl]-acrylic acid methyl ester;

(02) 3-methoxy-2-[α-{[(α-cyclopropyl-3,4-(difluoromethylenedioxy)benzyl)imino]-oxy}-o-tolyl]-acrylic acid methyl ester;

(03) 2-[α-{[(α-methyl-3-bromobenzyl)imino]-oxy}-o-tolyl]-glyoxylic acid methyl ester O-methyloxime;

(04) 2-[α-{[(α-cyclopropyl-3,4-methylenedioxybenzyl)imino]-oxy}-o-tolyl]-glyoxylic acid methyl ester O-methyloxime;

(05) 3-methoxy-2-[α{[(α-methyl-3-propargyloxybenzyl)imino]-oxy}-o-tolyl]-acrylic acid methyl ester;

(06) 2-[α-{[(α-methyl-3,4-(difluoromethylenedioxy)benzyl)imino]-oxy}-o-tolyl]-glyoxylic acid methyl ester O-methyloxime;

(07) 3-methoxy-2-[α-{[(α-cyclopropyl-3,4-methylenedioxybenzyl)imino]-oxy}-o-tolyl]-acrylic acid methyl ester;

(08) 2-[α-{[(α-methyl-3-propargyloxybenzyl)imino]-oxy}-o-tolyl]-glyoxylic acid methyl ester O-methyloxime;

(09) 2-[α-{[(α-cyclopropyl-4-fluorobenzyl)imino]-oxy}-o-tolyl]-glyoxylic acid methyl ester O-methyloxime;

(10) 2-[α-{[(α-methyl-4-fluoro-3-trifluoromethyl-benzyl)imino]-oxy}-o-tolyl]-glyoxylic acid methyl ester O-methyloxime;

(11) 3-methoxy-2-[α-{[(1-(β-naphthyl)ethyl)imino]-oxy}-o-tolyl]-acrylic acid methyl ester;

(12) 3-methoxy-2-[α-{[(α-methyl-3,4-methylenedioxybenzyl)imino]-oxy}-o-tolyl]-acrylic acid methyl ester;

(13) 2-[α-{[(α-methyl-3-chlorobenzyl)imino]-oxy}-o-tolyl]-glyoxylic acid methyl ester O-methyloxime;

(14) 3-methoxy-2-[α-{[(α-methyl-3,4-ethylenedioxybenzyl)imino]-oxy}-o-tolyl]-acrylic acid methyl ester;

(15) 2-[α-{[(α-cyclopropyl-4-chlorobenzyl)imino]-oxy}-o-tolyl]-glyoxylic acid methyl ester O-methyloxime;

(16) 3-methoxy-2-[α-{[(α-cyclopropyl-3-chlorobenzyl)imino]-oxy}-o-tolyl]-acrylic acid methyl ester;

(17) 2-[α-{[(α-cyclopropyl-3-trifluoromethylbenzyl)imino]-oxy}-o-tolyl]-glyoxylic acid methyl ester O-methyloxime;

(18) 3-methoxy-2-[α-{[(α-methyl-3-trifluoromethoxy-benzyl)imino]-oxy}-o-tolyl]-acrylic acid methyl ester;

(19) 2-[α-{[(α-methyl-3,4-methylenedioxybenzyl)imino]-oxy}-o-tolyl]-glyoxylic acid methyl ester O-methyloxime;

(20) 2-[α-{[(α-cyclopropyl-3,4-(difluoromethylenedioxy)benzyl)imino]-oxy}-o-tolyl]-glyoxylic acid methyl ester O-methyloxime;

(21) 2-[α-{[(α-methyl-3,4-ethylenedioxybenzyl)imino]-oxy}-o-tolyl]-glyoxylic acid methyl ester O-methyloxime;

(22) 3-methoxy-2-[α-{[(1-(2,3-dihydro-2,2,3-trifluoro-1,4-benzodioxan-6-yl)ethyl)-imino]-oxy}-o-tolyl]-acrylic acid methyl ester;

(23) 2-[α-{[(1-(2,3-dihydro-2,2,3-trifluoro-1,4-benzodioxan-6-yl)ethyl)-imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester;

(25) 2-[α-{[(α-methyl-4-chlorobenzyl)imino]-oxy}-o-tolyl]-glyoxylic acid methyl ester O-methyloxime;

(26) 3-methoxy-2-[α-{[(α-methyl-4-chlorobenzyl)imino]-oxy}-o-tolyl]-acrylic acid methyl ester;

(27) 3-methoxy-2-[α-{[(α-methyl-3-bromobenzyl)imino]-oxy}-o-tolyl]-acrylic acid methyl ester;

(28) 2-[α-{[(1-(β-naphthyl)ethyl)imino]-oxy}-o-tolyl]-glyoxylic acid methyl ester O-methyloxime;

(29) 3-methoxy-2-[α-{[(α-methyl-3,4-(difluoromethylenedioxy)benzyl)imino]-oxy}-o-tolyl]-acrylic acid methyl ester;

(30) 3-methoxy-2-[α-{[(α-cyclopropyl-4-fluorobenzyl)imino]-oxy}-o-tolyl]-acrylic acid methyl ester;

(31) 3-methoxy-2-[α-{[(α-methyl-4-fluoro-3-trifluoromethyl-benzyl)imino]-oxy}-o-tolyl]-acrylic acid methyl ester;

(32) 2-[α-{[(α-methyl-3-trifluoromethoxy-benzyl)imino]-oxy}-o-tolyl]-glyoxylic acid methyl ester O-methyloxime;

(33) 2-[α-{[(α-cyclopropyl-3-chlorobenzyl)imino]-oxy}-o-tolyl]-glyoxylic acid methyl ester O-methyloxime;

(34) 3-methoxy-2-[α-{[(α-methyl-3-chlorobenzyl)imino]-oxy}-o-tolyl]-acrylic acid methyl ester;

(35) 2-[α-{[(α-methyl-3-trifluoromethyl-benzyl)imino]-oxy}-o-tolyl]-glyoxylic acid methyl ester O-methyloxime;

(36) 3-methoxy-2-[α-{[(α-cyclopropyl-4-chlorobenzyl)imino]-oxy}-o-tolyl]-acrylic acid methyl ester;

(37) 2-[α-{[(α-cyclopropyl-4-trifluoromethyl-benzyl)imino]-oxy}-o-tolyl]-glyoxylic acid methyl ester O-methyloxime; and

(38) 2-[α-{[(α-cyclopropyl-4-trifluoromethoxy-benzyl)imino]-oxy}-o-tolyl]-glyoxylic acid methyl ester O-methyloxime.

Of those compounds, preference is given especially to the following:

(25) 2-[α-{[(α-methyl-4-chlorobenzyl)imino]-oxy}-o-tolyl]-glyoxylic acid methyl ester O-methyloxime;

(03) 2-[α-{[(α-methyl-3-bromobenzyl)imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester;

(06) 2-[α-{[(α-methyl-3,4-(difluoromethylenedioxy)benzyl)imino]-oxy}-o-tolyl]-glyoxylic acid methyl ester O-methyloxime;

(32) 2-[α-{[(α-methyl-3-trifluoromethoxy-benzyl)imino]-oxy}-o-tolyl]-glyoxylic acid methyl ester O-methyloxime;

(29) 3-methoxy-2-[α-{[(α-methyl-3,4-(difluoromethylenedioxy)benzyl)imino]-oxy}-o-tolyl]-acrylic acid methyl ester;

(09) 2-[α-{[(α-cyclopropyl-4-fluorobenzyl)imino]-oxy}-o-tolyl]-glyoxylic acid methyl ester O-methyloxime;

(26) 3-methoxy-2-[α-{[(α-methyl-4-chlorobenzyl)imino]-oxy}-o-tolyl]-acrylic acid methyl ester;

(34) 3-methoxy-2-[α-{[(α-methyl-3-chlorobenzyl)imino]-oxy}-o-tolyl]-acrylic acid methyl ester;

(18) 3-methoxy-2-[α-{[(α-methyl-3-trifluoromethoxy-benzyl)imino]-oxy}-o-tolyl]-acrylic acid methyl ester;

(35) 2-[α-{[(α-methyl-3-trifluoromethyl-benzyl)imino]-oxy}-o-tolyl]-glyoxylic acid methyl ester O-methyloxime;

(15) 2-[α-{[(α-cyclopropyl-4-chlorobenzyl)imino]-oxy}-o-tolyl]-glyoxylic acid methyl ester O-methyloxime;

(36) 3-methoxy-2-[α-{[(α-cyclopropyl-4-chlorobenzyl) imino]-oxy}-o-tolyl]-acrylic acid methyl ester;

(27) 3-methoxy-2-[α-{[(α-methyl-3-bromobenzyl) imino]-oxy}-o-tolyl]-acrylic acid methyl ester;

(37) 2-[α-{[(α-cyclopropyl-4-trifluoromethyl-benzyl) imino]-oxy}-o-tolyl]-glyoxylic acid methyl ester O-methyloxime; and

(38) 2-[α-{[(α-cyclopropyl-4-trifluoromethoxy-benzyl) imino]-oxy}-o-tolyl]-glyoxylic acid methyl ester O-methyloxime.

Especially advantageous mixtures are obtained when a component of formula I is used together with any one of the following components II: propiconazol, cyproconazol, epoxyconazol, tebuconazol or tetraconazol.

The compound mixtures I+II according to the invention have very advantageous properties for the protection of plants against attack by diseases.

The compound mixtures of the invention can be used to inhibit or to destroy the microorganisms occurring on plants or on parts of plants (the fruit, blossom, leaves, stems, tubers or roots) of various crops of useful plants, while at the same time parts of plants that grow later are also protected against such microorganisms. They can also be used as dressings in the treatment of plant propagation material, especially seed (fruit, tubers, grains) and plant cuttings (for example rice), to provide protection against fungal infections and against phytopathogenic fungi occurring in the soil. The compound mixtures according to the invention are distinguished by the fact that they are especially well tolerated by plants and are environmentally friendly.

The compound mixtures are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genera Hemileia, Rhizoctonia, Puccinia); Fungi imperfecti (e.g. Botrytis, Helminthosporium, Rhynchosporium, Fusarium, Septoria, Cercospora, Alternaria, Pyricularia and especially Pseudocercosporella herpotrichoides); and Oomycetes (e.g. Phytophthora, Peronospora, Bremia, Pythium and Plasmopara).

Target crops to be protected within the scope of the present invention comprise, for example, the following species of plants: cereals: (wheat, barley, rye, oats, rice, sorghum and related species); beets: (sugar beet and fodder beet); pomes, stone fruit and soft fruit: (apples, pears, plums, peaches, almonds, cherries, strawberries, raspberries and blackberries); leguminous plants: (beans, lentils, peas and soybeans); oil plants: (rape, mustard, poppy, olives, sunflowers, coconut, castor oil plants, cocoa beans and groundnuts); cucumber plants: (marrows, cucumber and melons); fiber plants: (cotton, flax, hemp and jute); citrus fruit: (oranges, lemons, grapefruit and mandarins); vegetables: (spinach, lettuce, asparagus, cabbages, carrots, onions, tomatoes, potatoes and paprika); lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). That list does not represent any limitation.

The compound mixtures according to the invention are especially advantageous for applications in cereals, especially in wheat and barley; also in vines, rice, bananas, fruit and vegetables.

The mixtures of compounds of formulae I and II are generally used in the form of compositions. The compounds of formulae I and II can be applied to the area or plant to be treated, either simultaneously or in succession on the same day, together with, where appropriate, further carriers, surfactants or other application-promoting adjuvants customarily employed in formulation technology.

Suitable carriers and adjuvants may be solid or liquid and are substances ordinarily employed in formulation technology, for example natural or regenerated mineral substances, solvents, dispersants, wetting agents, tackifiers, thickeners, binders or fertilisers.

A preferred method of applying a compound mixture comprising at least one of each of compounds I and II is application to the parts of the plants that are above the soil, especially to the leaves (foliar application). The frequency and rate of application depend on the biological and climatic living conditions of the pathogens. The compounds can, however, also penetrate the plants through the roots via the soil or water (systemic action) if the locus of the plant is impregnated with a liquid formulation (for example in rice culture), or if the compounds are introduced in solid form into the soil, e.g. in the form of granules (soil application). In order to treat the seed, the compounds of formulae I and II may also be applied to the seeds (coating) either by impregnating the tubers or grains with a liquid formulation of each of the compounds in succession or by coating them with an already combined wet or dry formulation. In addition, in special cases, other methods of application to plants are possible, e.g. treatment directed at the buds or the fruit.

The compounds of the combination are used in unmodified form or preferably together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts or granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the compound mixture are generally from 50 g to 2 kg a.i./ha, preferably from 100 g to 1000 g a.i./ha, especially from 150 g to 700 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as xylene mixtures or substituted naphthalenes, phthalates, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, and vegetable oils or epoxidised vegetable oils, such as epoxidised coconut oil or soybean oil; and water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated absorptive carriers are porous types, for example pumice, broken brick, sepiolite or bentonite; and suitable nonsorbent carriers are e.g. calcite or sand. In addition, a great number of pregranulated materials of inorganic or organic nature can be used, such as especially dolomite or pulverised plant residues.

Depending on the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

Especially advantageous application-promoting adjuvants are also natural or synthetic phospholipids from the series of cephalins and lecithins, such as phosphatidylethanolamine, phosphatidylserine, phosphatidylglycerol and lysolecithin.

The agrochemical compositions generally comprise 0.1 to 99%, preferably 0.1 to 95%, of compounds of formulae I and II, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

Such formulations form part of the present invention.

The Examples that follow serve to illustrate the invention, "active ingredient" denoting a mixture of compound I and compound II in a specific mixing ratio.

FORMULATIONS EXAMPLES

| Wettable powders | a) | b) | c) |
|---|---|---|---|
| active ingredient | | | |
| [I:II = 4:1(a), 1:11(b), 3:2(c)] | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

| Emulsifiable concentrate | |
|---|---|
| active ingredient (I:ll = 3:7) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in crop protection, can be obtained from this concentrate by dilution with water.

| Dusts | a) | b) | c) |
|---|---|---|---|
| active ingredient | | | |
| [I:II = 1:4(a); 5:1(b) and 1:1(c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (I:II = 14:1) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient (I:II = 7:1) | 8% |
| polyethylene glycol (mol. wt. 200) | 3% |
| kaolin | 89% |

(mol. wt. = molecular weight)

The finely ground active ingredient is uniformly applied, in a mixer, to the kaolin moistened with polyethylene glycol. Non-dusty coated granules are obtained in this manner.

| Suspension concentrate | |
|---|---|
| active ingredient | |
| (I:II = 3:1) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% aqueous emulsion) | 1% |
| water | 32% |

The finely ground active ingredient is intimately mixed with the adjuvants, giving a suspension concentrate from which suspensions of any desired dilution can be obtained by dilution with water. Such dilutions can be used to treat living plants and plant propagation material by spraying, pouring or immersion and to protect them against infestation by microorganisms.

BIOLOGICAL EXAMPLES

A synergistic effect exists whenever the action of the active ingredient combination is greater than the sum of the actions of the individual components.

The action E to be expected for a given active ingredient combination obeys the COLBY formula and can be calculated as follows (COLBY, S. R. "Calculating synergistic and antagonistic responses of herbicide combination". Weeds, Vol. 15, pages 20–22; 1967);

ppm=milligram of active ingredient (=ai) per liter of spray mixture

X=% action by active ingredient I using p ppm of active ingredient

Y=% action by active ingredient II using q ppm of active ingredient and

E=the expected action of active ingredients I+II using p+q ppm of active ingredient (additive action):

according to Colby:

$$E = X + Y - \frac{X \cdot Y}{100}.$$

If the action (O) actually observed is greater than the expected action (E), then the action of the combination is superadditive, i.e. there is a synergistic effect.

O/E=synergy factor (SF).

In the Examples that follow, the infestation of the untreated plants is said to be 100%, which corresponds to an action of 0%.

EXAMPLE B-1

Action Against Puccinia Recondita on Wheat a) Residual-protective action:

6 days after sowing, wheat plants are sprayed to drip point with an aqueous spray mixture prepared from a wettable powder formulation of the test compound mixture and are infected 24 hours later with a uredospore suspension of the fungus. After an incubation period of 48 hours (conditions: 95 to 100% relative humidity at 20°), the plants are placed in a greenhouse at 22°. Evaluation of fungus infestation is made 12 days after infection.

b) Systemic action:

5 days after sowing, wheat plants are watered with an aqueous spray mixture prepared from a wettable powder formulation of the test compound mixture. Care is taken that the spray mixture does not come into contact with the parts of the plants above the soil. After 48 hours the plants are infected with a uredospore suspension of the fungus. After an incubation period of 48 hours (conditions: 95 to 100% relative humidity at 20°), the plants are placed in a greenhouse at 22°. Evaluation of fungus infestation is made 12 days after infection.

In particular, compound mixtures wherein component I is

(29) 3-methoxy-2-[α-{[(α-methyl-3,4-(difluoromethylenedioxy)benzyl)imino]-oxy}-o-tolyl]-acrylic acid methyl ester;

(18) 3-methoxy-2-[α-{[(α-methyl-3-trifluoromethoxy-benzyl)imino]-oxy}-o-tolyl]-acrylic acid methyl ester;

(32) 2-[α-{[(α-methyl-3-trifluoromethoxy-benzyl)imino]-oxy}-o-tolyl]-glyoxylic acid methyl ester O-methyloxime;

(15) 2-[α-{[(α-cyclopropyl-4-chlorobenzyl)imino]-oxy}-o-tolyl]-glyoxylic acid methyl ester O-methyloxime;

(35) 2-[α-{[(α-methyl-3-trifluoromethyl-benzyl)imino]-oxy}-o-tolyl]-glyoxylic acid methyl ester O-methyloxime;

(6) 2-[α-{[(α-methyl-3,4-(difluoromethylenedioxy)benzyl)imino]-oxy}-o-tolyl]-glyoxylic acid methyl ester O-methyloxime; or

(37) 2-[α-{[(α-cyclopropyl-4-trifluoromethyl-benzyl)imino]-oxy}-o-tolyl]-glyoxylic acid methyl ester O-methyloxime;

exhibit good synergistic action.

EXAMPLE B-2

Action Against Plasmopara Viticola on Vines

Vine seedlings in the 4–5 leaf stage are sprayed to drip point with an aqueous spray mixture prepared from a wettable powder formulation of the test compound mixture. After 24 hours the treated plants are infected with a sporangia suspension of the fungus. Evaluation of fungus infestation is made 6 days after infection, during which time conditions of 95–100% relative humidity and a temperature of 20° have been maintained.

In particular, compound mixtures wherein component I is

(29) 3-methoxy-2-[α-{[(α-methyl-3,4-(difluoromethylenedioxy)benzyl)imino]-oxy}-o-tolyl]-acrylic acid methyl ester;

(18) 3-methoxy-2-[α-{[(α-methyl-3-trifluoromethoxy-benzyl)imino]-oxy}-o-tolyl]-acrylic acid methyl ester;

(32) 2-[α-{[(α-methyl-3-trifluoromethoxy-benzyl)imino]-oxy}-o-tolyl]-glyoxylic acid methyl ester O-methyloxime;

(15) 2-[α-{[(α-cyclopropyl-4-chlorobenzyl)imino]-oxy}-o-tolyl]-glyoxylic acid methyl ester O-methyloxime; or (6) 2-[α-{[(α-methyl-3,4-(difluoromethylenedioxy)benzyl)imino]-oxy}-o-tolyl]-glyoxylic acid methyl ester O-methyloxime;

exhibit good synergistic action.

EXAMPLE B-3

Residual-Protective Action Against Venturia Inaequalis on Apples

Apple cuttings with 10–20 cm long fresh shoots are sprayed to drip point with an aqueous spray mixture prepared from a wettable powder formulation of the test compound mixture and are infected 24 hours later with a conidia suspension of the fungus. The plants are incubated for 5 days at 90 to 100% relative humidity and are placed for a further 10 days in a greenhouse at 20 to 24°. Fungus infestation is evaluated 12 days after infection. The compound mixtures according to the invention exhibit clearly enhanced action.

EXAMPLE B-4

Action Against Erysiphe Graminis on Barley a) Residual-protective action:

Barley plants about 8 cm in height are sprayed to drip point with an aqueous spray mixture prepared from a wettable powder formulation of the test compound mixture and are dusted 3 to 4 hours later with conidia of the fungus. The infected plants are placed in a greenhouse at 22°. Fungus infestation is evaluated 12 days after infection.

b) Systemic action:

Barley plants about 8 cm in height are watered with an aqueous spray mixture prepared from a wettable powder formulation of the test compound mixture. Care is taken that the spray mixture does not come into contact with the parts of the plants above the soil. The plants are dusted 48 hours later with conidia of the fungus. The infected plants are placed in a greenhouse at 22°. Evaluation of fungus infestation is made 12 days after infection.

In particular, compound mixtures wherein component I is (6) 2-[α-{[(α-methyl-3,4-(difluoromethylenedioxy)benzyl)imino]-oxy}-o-tolyl]-glyoxylic acid methyl ester O-methyloxime;

(32) 2-[α-{[(α-methyl-3-trifluoromethoxy-benzyl)imino]-oxy}-o-tolyl]-glyoxylic acid methyl ester O-methyloxime;

(15) 2-[α-{[(α-cyclopropyl-4-chlorobenzyl)imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester;

(35) 2-[α-{[(α-methyl-3-trifluoromethyl-benzyl)imino]-oxy}-o-tolyl]-glyoxylic acid methyl ester O-methyloxime;

(29) 3-methoxy-2-[α-{[(α-methyl-3,4-(difluoromethylenedioxy)benzyl)imino]-oxy}-o-tolyl]-acrylic acid methyl ester;

(18) 3-methoxy-2-[α-{[(α-methyl-3-trifluoromethoxy-benzyl)imino]-oxy}-o-tolyl]-acrylic acid methyl ester;

(36) 3-methoxy-2-[α-{[(α-cyclopropyl-4-chlorobenzyl)imino]-oxy}-o-tolyl]-acrylic acid methyl ester; or

(38) 2-[α-{[(α-cyclopropyl-4-trifluoromethoxy-benzyl)imino]-oxy}-o-tolyl]-glyoxylic acid methyl ester O-methyloxime, exhibit good synergistic action.

EXAMPLE B-5

Action Against Phytophthora Infestans on Tomato Plants a) Curative action:

After a cultivation period of 3 weeks, tomato plants of the "Red Gnome" variety are sprayed with a zoospore suspension of the fungus and incubated in a cabinet at 18 to 20° and 100% humidity. Humidification is stopped after 24 hours. When the plants have dried, they are sprayed with a mixture comprising the test compounds formulated as a wettable powder. After the spray coating has dried, the plants are again placed in the humidity cabinet for 4 days. The activity of the test compounds is evaluated on the basis of the number and size of the typical leaf specks that have appeared after that time.

b) Preventive-systemic action:

The test compound mixture formulated as a wettable powder is applied to the soil surface of three-week-old tomato plants of the "Red Gnome" variety planted in pots. After a 3-day waiting period, the undersides of the leaves of the plants are sprayed with a zoospore suspension of Phytophthora infestans. The plants are then kept in a spray cabinet for 5 days at 18 to 20° C. and 100% humidity. After that time, typical leaf specks form, the number and size of which are used to evaluate the activity of the test compounds.

In particular, compound mixtures wherein component I is (6) 2-[α-{[(α-methyl-3,4-(difluoromethylenedioxy) benzyl)imino]-oxy}-o-tolyl]-glyoxylic acid methyl ester O-methyloxime;

(32) 2-[α-{[(α-methyl-3-trifluoromethoxy-benzyl) imino]-oxy}-o-tolyl]-glyoxylic acid methyl ester O-methyloxime;

(15) 2-[α-{[(α-cyclopropyl-4-chlorobenzyl)imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester; or

(36) 3-methoxy-2-[α-{[(α-cyclopropyl-4-chlorobenzyl) imino]-oxy}-o-tolyl]-acrylic acid methyl ester, exhibit good synergistic action.

EXAMPLE B-6

Residual-Protective Action Against Cercospora Arachidicola on Groundnuts 10 to 15 cm high groundnut plants are sprayed to drip point with an aqueous spray mixture and are infected 48 hours later with a conidia suspension of the fungus. The plants are incubated for 72 hours at 21° and high humidity and are then placed in a greenhouse until the typical leaf specks appear. The activity of the test compound is evaluated 12 days after infection and is based on the number and size of the leaf specks.

In particular, compound mixtures wherein component I is

(32) 2-[α-{[(α-methyl-3-trifluoromethoxy-benzyl) imino]-oxy}-o-tolyl]-glyoxylic acid methyl ester O-methyloxime;

(35) 2-[α-{[(α-methyl-3-trifluoromethyl-benzyl)imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester;

(15) 2-[α-{[(α-cyclopropyl-4-chlorobenzyl)imino]-oxy}-o-tolyl]-glyoxylic acid methyl ester O-methyloxime;

(18) 3-methoxy-2-[α-{[(α-methyl-3-trifluoromethoxy-benzyl)imino]-oxy}-o-tolyl]-acrylic acid methyl ester; or

(36) 3-methoxy-2-[α-{[(α-cyclopropyl-4-chlorobenzyl) imino]-oxy}-o-tolyl]-acrylic acid methyl ester, exhibit good synergistic action.

EXAMPLE B7

Action Against Pyricularia Oryzae on Rice Plants a) Residual-protective action:

After a cultivation period of 2 weeks, rice plants are sprayed to drip point with an aqueous spray mixture of the active ingredients. After 48 hours the treated plants are infected with a conidia suspension of the fungus. Evaluation of fungus infestation is made 5 days after infection, during which time conditions of 95–100% relative humidity and a temperature of 22° have been maintained.

b) Systemic action:

2-week-old rice plants are watered with an aqueous spray mixture of the active ingredients. Care is taken that the spray mixture does not come into contact with the parts of the plants above the soil. The pots are then filled with water so that the lowermost parts of the stems of the rice plants stand in water. After 96 hours, the treated plants are infected with a conidia suspension of the fungus and then maintained for 5 days at 95–100% relative humidity and a temperature of 24° C.

In particular, compound mixtures wherein component II is propiconazol, cyproconazol, epoxyconazol, tebuconazol or tetraconazol exhibit good synergistic action.

EXAMPLE B-8

Action Against Botrytis Cinerea on Apple Fruits

Residual-protective action:

Artificially damaged apples are treated by dropping a spray mixture of the active ingredients onto the damaged sites. The treated fruits are then inoculated with a spore suspension of the fungus and are incubated for one week at high humidity and about 20° C. The fungicidal activity of the test compound is derived from the number of damaged sites that have rotted.

In particular, compound mixtures wherein component I is

(32) 2-[α-{[(α-methyl-3-trifluoromethoxy-benzyl) imino]-oxy}-o-tolyl]-glyoxylic acid methyl ester O-methyloxime;

(35) 2-[α-{[(α-methyl-3-trifluoromethyl-benzyl)imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester;

(15) 2-[α-{[(α-cyclopropyl-4-chlorobenzyl)imino]-oxy}-o-tolyl]-glyoxylic acid methyl ester O-methyloxime;

(18) 3-methoxy-2-[α-{[(α-methyl-3-trifluoromethoxy-benzyl)imino]-oxy}-o-tolyl]-acrylic acid methyl ester; or

(36) 3-methoxy-2-[α-{[(α-cyclopropyl-4-chlorobenzyl)imino]-oxy}-o-tolyl]-acrylic acid methyl ester, and wherein component II is cyproconazol, epoxyconazol, penconazol, pyrifenox or tetraconazol, exhibit good synergistic action.

EXAMPLE B-9

Action Against Helminthosporium Gramineum

Wheat grains are contaminated with a spore suspension of the fungus and allowed to dry. The contaminated grains are dressed with a suspension of the test compound mixture. After two days the grains are sown on suitable agar dishes and four days later the development of the fungus colonies around the grains is assessed. The number and size of the fungus colonies are used to evaluate the test compound.

In particular, compound mixtures wherein component II is propiconazol, epoxyconazol, tebuconazol, tetraconazol or prochloraz exhibit good synergistic action.

EXAMPLE B-10

Action Against Fusarium Nivale on Rye

Rye of the Tetrahell variety that is naturally infected with Fusarium nivale is dressed in a roller mixer with the test fungicide mixture.

The infected and treated rye is sown in October in the open with a seeder in plots 3 meters long and in 6 rows. Three replicates are carried out with each concentration.

Until evaluation of the infestation is made, the test crop is cultivated under normal field conditions (preferably in a region with unbroken snow cover during the winter months). In order to evaluate the phytotoxicity, the emergence is assessed in the autumn and the crop density/number of plants per unit area is assess in the spring.

To determine the activity of the test compounds, the percentage of plants infested by Fusarium is assessed in the spring immediately after the snow has melted.

In particular, compound mixtures wherein component I is

(32) 2-[α-{[(α-methyl-3-trifluoromethoxy-benzyl)imino]-oxy}-o-tolyl]-glyoxylic acid methyl ester O-methyloxime;

(15) 2-[α-{[(α-cyclopropyl-4-chlorobenzyl)imino]-oxy}-o-tolyl]-glyoxylic acid methyl ester O-methyloxime;

(18) 3-methoxy-2-[α-{[(α-methyl-3-trifluoromethoxy-benzyl)imino]-oxy}-o-tolyl]-acrylic acid methyl ester; or (6) 2-[α-{[(α-methyl-3,4-(difluoromethylenedioxy)benzyl)imino]-oxy}-o-tolyl]-glyoxylic acid methyl ester O-methyloxime, and component II is propiconazol, epoxyconazol, tebuconazol, tetraconazol or prochloraz, exhibit good synergistic action.

EXAMPLE B-11

Action Against Septoria Nodorum on Wheat

Wheat plants are sprayed in the 3-leaf stage with a spray mixture prepared from a wettable powder formulation of the test compounds. 24 hours later, the treated plants are infected with a conidia suspension of the fungus. The plants are then incubated for 2 days at 90–100% relative humidity and are placed in a greenhouse for a further 10 days at 20–24° C. Fungus infestation is evaluated 13 days after infection.

In particular, compound mixtures wherein component I is

(32) 2-[α-{[(α-methyl-3-trifluoromethoxy-benzyl)imino]-oxy}-o-tolyl]-glyoxylic acid methyl ester O-methyloxime;

(35) 2-[α-{[(α-methyl-3-trifluoromethyl-benzyl)imino]-oxy}-o-tolyl]-glyoxylic acid methyl ester O-methyloxime;

(24) 3-methoxy-2-[α-{[(α-methyl-3-trifluoromethyl-benzyl)imino]-oxy}-o-tolyl]-acrylic acid methyl ester;

(15) 2-[α-{[(α-cyclopropyl-4-chlorobenzyl)imino]-oxy}-o-tolyl]-glyoxylic acid methyl ester O-methyloxime;

(18) 3-methoxy-2-[α-{[(α-methyl-3-trifluoromethoxy-benzyl)imino]-oxy}-o-tolyl]-acrylic acid methyl ester; or

(36) 3-methoxy-2-[α-{[(α-cyclopropyl-4-chlorobenzyl)imino]-oxy}-o-tolyl]-acrylic acid methyl ester, and wherein component II is propiconazol, tebuconazol, tetraconazol, difenoconazol, bromuconazol or prochloraz, exhibit good synergistic action.

What is claimed is:

1. A composition comprising at least two active ingredient components in synergistic microbicidally effective combined amounts together with a suitable carrier, wherein component I is a compound of formula I

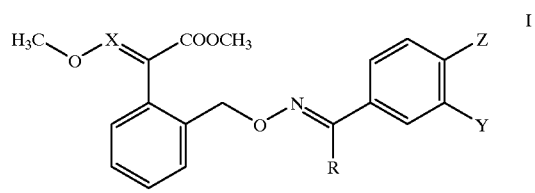

wherein:
X is N;
R is $CH_3$;
Y is $CF_3$;
Z is H;
and wherein component II is a compound selected from the group consisting of
A) 1-[2-(2,4-dichlorophenyl)-4-propyl-1,3-dioxolan-2-ylmethyl]-1H-1,2,4-triazole;
B) 1-{2-[2-chloro-4-(4-chlorophenoxy)-phenyl]-4-methyl-1,3-dioxolan-2-ylmethyl}-1H-1,2,4-triazole;
C) 1-[2-(2,4-dichlorophenyl)pentyl-1H-1,2,4-triazole;
D) α-[2-(4-chlorophenyl)ethyl]-α-(1,1-dimethylethyl)-1H-1,2,4-triazole-1-ethanol;
E) 1-[[3-(2-chlorophenyl)-2-(4-fluorophenyl)oxiran-2-yl]methyl]-1H-1,2,4-triazole;
F) α-(4-chlorophenyl)-α-(1-cyclopropylethyl)-1H-1,2,4-triazole-1-ethanol;
G) α-butyl-α-(2,4-dichlorophenyl)-1H-1,2,4-triazole-1-ethanol;
H) 4-(4-chlorophenyl)-2-phenyl-2-(1,2,4-triazol-1-ylmethyl)-butyronitrile;
J) 1-{[bis(4-fluorophenyl)methylsilyl]methyl}-1H-1,2,4-triazole;
K) 5-(4-chlorobenzyl)-2,2-dimethyl-1-(1H-1,2,4-triazol-1-ylmethyl)-cyclopentanol;

L) 2-(2,4-dichlorophenyl)-3-(1H-1,2,4-triazol-1-yl) propyl-1,1,2,2-tetrafluoroethyl ether;

M) 1-[4-bromo-2-(2,4-dichlorophenyl) tetrahydrofurfuryl]-1H-1,2,4-triazole;

N) 3-(2,4-dichlorophenyl)-6-fluoro-2-(1H-1,2,4-triazol-1-yl)quinazolin-4(3H)-one; and

[O) N-propyl-N-2-(2,4,6-trichlorophenoxy)ethyl] imidazole-1-carboxide;

P) 2',4'-dicloro-2-(3-pyridyl)acetophenons O-methyloxime;] and

Q) 2-p-chlorophenyl-2-(1H-1,2,4-triazol-1-ylmethyl) hexanenitrile;

or a salt or a metal complex thereof, and wherein the ratio by weight of I:II is 10:1 to 1:10.

2. The composition according to claim 1, wherein component II is compound A) 1-[2-(2,4-dichlorophenyl)-4-propyl-1,3-dioxolan-2-ylmethyl]-1H-1,2,4-triazole.

3. The composition according to claim 1, wherein the ratio by weight of I:II=10:1 to 1:5.

4. The composition according to claim 1, wherein the ratio by weight of I:II=10:1 to 1:3.

5. A method of controlling and preventing plant diseases, wherein, in any desired order or simultaneously, a site infested by or at risk of infestation by disease causing fungi is treated with a synergistic fungicidally effective combined amounts of component I and component II according to claim 1.

6. The method according to claim 5, wherein cereal is treated.

7. The method according to claim 5, wherein plant propagation material is treated.

8. The method according to claim 5 wherein the site infested or at risk of infestation is selected from the group consisting of plants, plant parts, seeds, or their locus, individually or in any combination.

* * * * *